United States Patent [19]

van Eikeren et al.

[11] Patent Number: 5,071,561
[45] Date of Patent: Dec. 10, 1991

[54] AMMONIA REMOVAL FROM MAMMALIAN CELL CULTURES

[75] Inventors: Paul van Eikeren; John M. Radovich, both of Bend, Oreg.

[73] Assignee: Bend Research, Inc., Bend, Oreg.

[21] Appl. No.: 315,477

[22] Filed: Feb. 24, 1989

[51] Int. Cl.$^5$ ............................................. B01D 61/24
[52] U.S. Cl. .................................... 210/645; 210/651
[58] Field of Search ................... 210/321.41, 634, 638, 210/640, 639, 644-647, 649-655

[56] References Cited

U.S. PATENT DOCUMENTS

| | | | |
|---|---|---|---|
| 3,878,564 | 4/1975 | Yao et al. | 210/321.4 |
| 4,268,279 | 3/1981 | Shindo et al. | 55/16 |

OTHER PUBLICATIONS

Ono et al., 94 *J. Biochem.* 1493 (Jun. 1983).

*Primary Examiner*—Frank Sever
*Attorney, Agent, or Firm*—Chernoff, Vilhauer, McClung & Stenzel

[57] ABSTRACT

A supported-fluid membrane process for the removal of inhibitory ammonia formed during the culturing of mammalian cells is disclosed.

10 Claims, 2 Drawing Sheets

AMMONIA REMOVAL FROM MAMMALIAN CELL CULTURES

The government has rights in this invention under National Science Foundation Award No. ISI-870538.

BACKGROUND OF THE INVENTION

Ammonia is a toxic waste by-product of cell metabolism which, as it accumulates in an aqueous cell-growth medium during the culturing of mammalian cells, inhibits cell growth and production of desired end products. A number of efforts have been made to solve this problem.

Currently, the aqueous cell growth medium with inhibitory levels of ammonia is simply discarded and replaced with fresh medium. This is inefficient as it requires additional equipment for sterilization and storage of fresh medium as well as the attendant replacement of costly serum in the fresh medium. Another proposed solution to the problem of ammonia accumulation has been the selection and use of a cell line that is more resistant to ammonia. See Ono et al., 94 *J. Biochem* 1493 (1983). However, there are relatively few cell lines that are known to be resistant to the inhibitory effects of ammonia. A more recent strategy for dealing with ammonia build-up has been strict control of glutamine (a primary source of ammonia) in the culture medium. See Glacken et al., 6 *Bio/Technology* 1041 (1988). However, this method only reduced ammonia by 25-30%, while compromising the ability of the cells to use other essential amino acids.

What is needed therefore, is a method of removing ammonia from mammalian cell cultures that dispenses with replacement of medium and glutamine control, and that may be utilized with the known wide variety of existing cell lines.

SUMMARY OF THE INVENTION

The present invention involves application of gas transfer through a fluid supported in a hydrophobic polymeric membrane matrix to the aforementioned problem of toxic ammonia build-up in mammalian cell cultures and satisfies the foregoing needs by removing ammonia from an aqueous culture medium while permitting reuse of the medium. The process comprises the essential steps of: contacting the aqueous culture medium with one side of a supported-fluid membrane wherein the support is a microporous hydrophobic polymeric membrane matrix; and maintaining a strip solution in contact with the other side of said membrane, the strip solution comprising an aqueous solution having a $pH \leq 7.0$.

DETAILED DESCRIPTION OF THE INVENTION

According to the present invention, there is provided a method for quantitatively removing ammonia from aqueous mammalian cell cultures to non-inhibitory levels that is simple, that may be used with existing technology on a batch or continuous basis and that permits reuse of the cell culture medium after ammonia removal.

Figure 1:
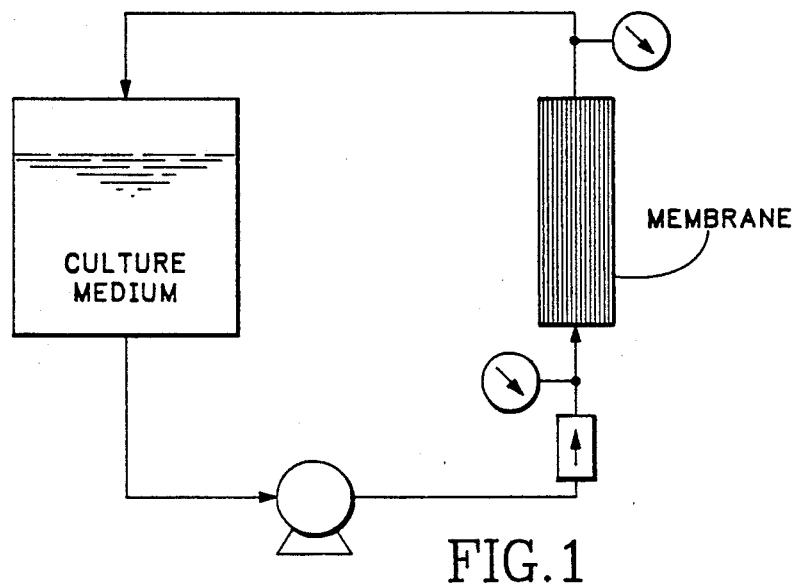
FIG. 1 is a schematic representation of the overall process of the present invention.

The basic overall process is shown schematically in FIG. 1 where an aqueous culture medium is shown as being removed from its container by a pump and circulated via a flow meter and pressure gauge to contact one side of a supported-fluid membrane in a microporous hydrophobic polymeric matrix, where the other side of the membrane is contacted by an acidic strip solution. The aqueous culture medium, stripped of ammonia, exits the membrane and is returned to its container via a second pressure gauge.

Figure 2:
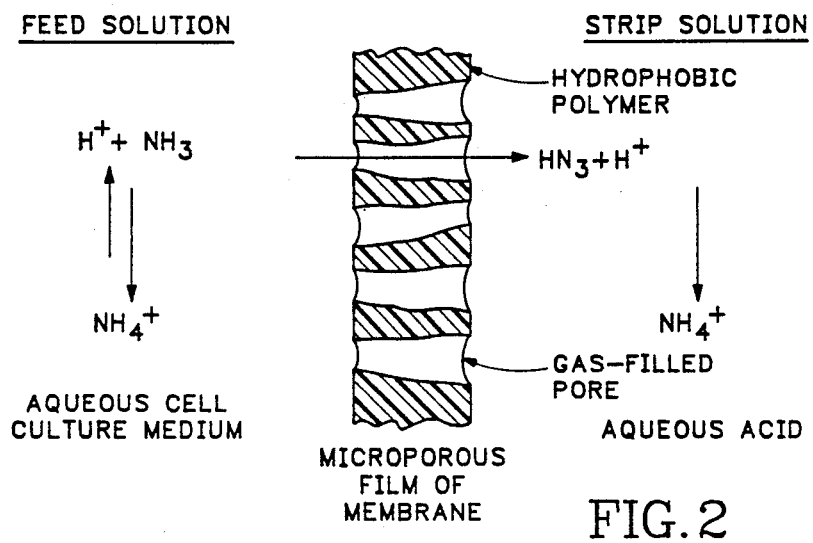
FIG. 2 is a schematic representation of ammonia diffusion across a representative membrane of the present invention.

FIG. 2 schematically illustrates the ammonia removal mechanism of the present invention by use of a supported-fluid membrane in a microporous hydrophobic polymeric support matrix wherein the fluid is a gas. There, the feed solution comprising the aqueous ammonia-containing cell culture medium is contacted with one side of a microporous hydrophobic polymeric membrane matrix having gas-filled pores; while any non-acidic or non-basic gas is suitable, the gas typically initially present in the pores is air. Since water cannot wet the hydrophobic polymer matrix, the aqueous feed and strip solutions do not mix one with the other. Ammonia diffuses through the gas medium in the micropores to the other side of the membrane where an acidic strip solution is maintained or circulated, the ammonia being immediately and irreversibly protonated at the gas/strip solution interface to form ammonium ion, which is "trapped" on the strip side of the membrane by virtue of the fact that, because the concentration of ammonia on the strip side of the membrane is near zero, the chemical potential between the feed side and strip sides strongly favors irreversible transport of ammonia from the feed side to the strip side.

Although FIG. 2 illustrates a supported-gas membrane, supported-liquid membranes will work in the process of the present invention as well. Suitable liquids for substantially filling the micropores of the polymeric membrane matrix include dialkyl phosphoric acids, dialkyl alkylphosphonic acids, aryl sulfonic acids, alkyl sulfonic acids, aryl carboxylic acids, alkyl carboxylic acids, aryl alcohols, alkyl alcohols, aryl amines, alkyl amines, and trialkylphosphine oxides, either alone or in combination with suitable solvents.

Suitable polymers for the hydrophobic polymeric microporous membrane matrices useful in the present invention include polyolefins such as polyethylene and polypropylene, polytetrafluoroethylene and copolymers thereof, poly(vinylidine fluoride), polysulfone, and polyethersulfone. The form of the membrane matrix may be hollow fibers, flat sheets, beads or polymer-coatings over bead substrates. Especially preferred membranes are polypropylene hollow fibers made and sold as "Celgard X-20" by Celanese Products of Charlotte, N.C., and as "Accurel PP" by Enka A. G. of West Germany.

Figure 3:
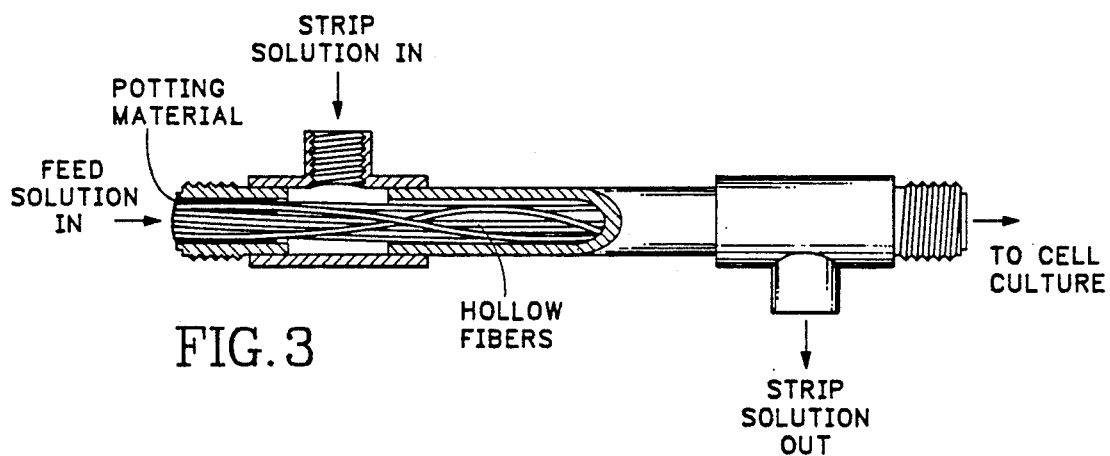
FIG. 3 is an exemplary membrane module.

FIG. 3 illustrates an especially preferred form of supported-fluid membrane module having multiple hollow fibers potted on each end and having inlet and outlet ports for circulating the feed and strip solutions. Although the strip solution is shown as being circulated via inlet and outlet ports, the shell side of the module may simply be filled with a strong acid solution, thus maintaining the strip solution in contact with the strip side of the membrane. And although lumen-side feed is preferred in hollow fibers, with the strip solution being circulated on the "shell" side or outside of the fibers, the reverse order may be used as well.

Although FIGS. 2 and 3 show the use of a hollow fiber membrane support matrix in the process of the present invention, membrane matrices in bead form or enclosing a bead of ammonia-absorbing material will work as well. Beads and membrane-coated beads are especially useful for the removal of ammonia produced during cell culture in shaker flasks, roller bottles, or small cell-culture fermentors. Exemplary membrane-coatable beads are of porous ceramic material and cation exchange resin material. Exemplary porous ceramic beads are those made and sold under the trade name "M40X Hollow Macrospheres" by 3M Company of St. Paul, Minn.; such beads may be filled with an aqueous acid solution of at least 0.25$\underline{M}$, then spray-coated with the microporous hydrophobic polymer membrane of the type described above. Preferred cation exchange resin beads are those of 16–50 mesh in the $H^+$ form having an acid content of at least 1 meq/ml; exemplary commercially available beads are the "Amberlite IRA-118H" beads by Rohm and Haas Company of Philadelphia, Pa.

Spray coating of the beads may be accomplished by mixing them with a solution of the hydrophobic polymer in a suitable solvent in a spray coating apparatus. An exemplary apparatus consists of an auger-feed system and a two-fluid air-atomizing external mixing nozzle, where the auger mixes beads with the polymer solution and delivers the beads one at a time to a nozzle where they mix with atomizing air. In a typical procedure, a 15 wt. % solution of Kynar 760 (poly(vinylidene fluoride), Pennwalt Corp., Philadelphia, Pa.) in dimethylacetamide is pumped at a rate of 10 ml/min to the auger-feed system. Beads are introduced at a rate of 0.5 g/min. The auger is set at a speed of 500 rpm and the atomizing air is supplied to the nozzle at 40 psi. The coated beads are sprayed upwards in a tower in which heated air is moving upwards. This arrangement provides a means to suspend the beads and provide sufficient suspension time for the formation of a dry polymer membrane 20 to 50 microns thick around the bead.

In operation of the process of the present invention, the aqueous culture medium feed may be circulated directly to the feed side of the membrane without dilution, pH adjustment or filtration. The pH of the culture medium is generally between 7.0 and 7.4. The pH of the acidic strip solution, preferably a strong acid solution such as sulfuric acid, may be $\leq 7.0$, preferably $\leq 5.0$. The process may be conducted at ambient to the slightly elevated temperatures of the culturing process.

REFERENCE EXAMPLE

Baby hamster kidney (BHK) cells were cultured in five flasks of an aqueous culture medium comprising Dubelcco's Modified Eagle's medium (DME) with 10 vol% calf serum in an incubator at 37° C., with various initial ammonia concentrations ranging from 0 to 13 m$\underline{M}$. The cultures were monitored over a period of 140 hours; the presence of ammonia was demonstrated to slow the cell growth rate by as much as 62% at the highest initial ammonia concentration.

EXAMPLE 1

Figure 4:
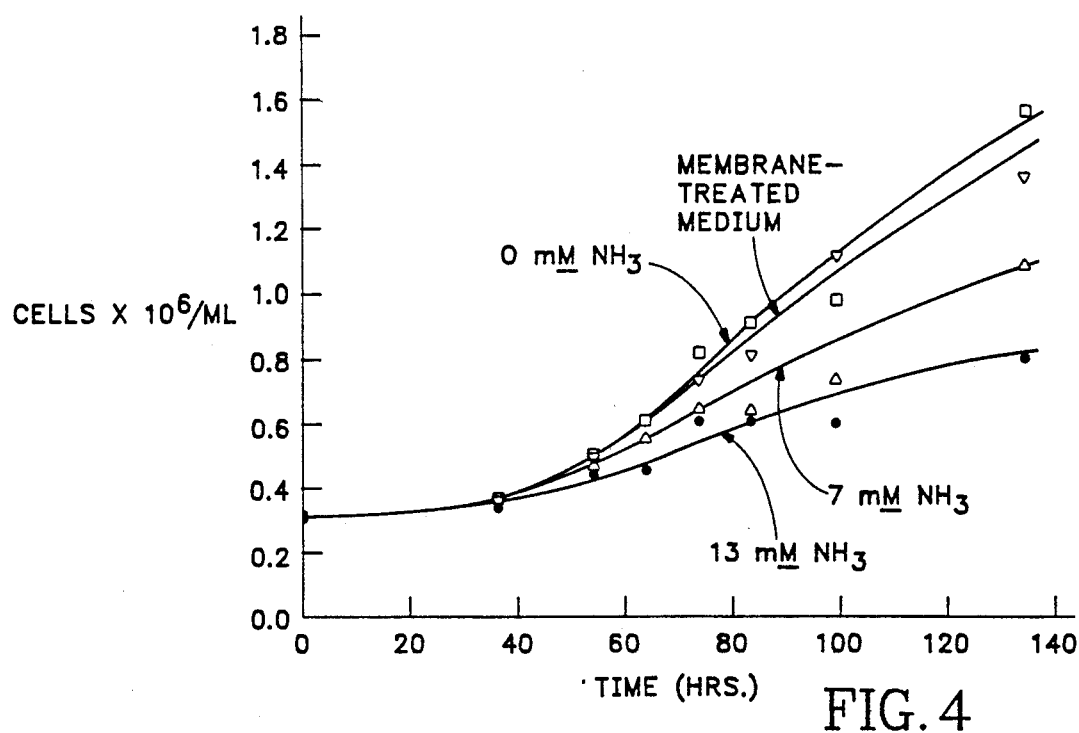
FIG. 4 is a graph showing mammalian cell count as a function of ammonia concentration in cell culture media.

The same BHK cells as those of the Reference Example were cultured in a fresh batch of the same culture medium having an initial ammonia concentration of 14 m$\underline{M}$, but having been membrane-treated as follows. The aqueous culture medium was circulated for 4.5 hours through the lumens of a supported-gas (air) membrane in a support comprising Celgard X-20 hollow fibers potted in a bundle in a module of the type shown in FIG. 3 at a rate of 19 L/hr, the fibers having 400 microns I.D., 450 microns O.D., 0.04 micron pore diameter, 40% porosity and a 220 psi burst pressure. The combined total membrane surface area was 2.0 sq ft. The shell of the module was filled with 0.5 $\underline{M}$ sulfuric acid, having a pH of 0.3, and immobilized therein by caps on the appropriate inlet an outlet ports. The circulation of the aqueous culture medium through the module reduced its ammonia concentration from 14 m$\underline{M}$ to 0.5 m$\underline{M}$. BHK cells were then grown in the so-treated medium at 37° C. for 140 hours and the cell count compared with those of certain of the Reference Example. The results, shown in the graph comprising FIG. 4, demonstrate that the membrane successfully removed inhibitory ammonia, yet, rather surprisingly, did not remove necessary nutrients or metabolites from the cell culture medium as demonstrated by the fact that cell growth in the membrane-treated medium was essentially the same as that of the ammonia-free untreated medium.

EXAMPLE 2

Hydrophobic polymer-coated ammonia-absorbing beads are prepared by coating Amberlite IRA-118H beads with a 20 microns-thick microporous hydrophobic poly(vinylidene fluoride) membrane matrix using the spray-coat technique previously described, then dried. The dry polymer-coated beads are then suspended in water for 24 hours to allow the interior of the bead to saturate with water (about 60 wt. %), then collected by filtration. The pores of the microporous hydrophobic polymeric matrix are filled with a solution of 33 wt. % trioctylphosphine oxide in hexadecane by immersing them in the solution. The loaded beads are then collected by filtration on a fritted-glass filter and washed with water to remove excess organic liquid, leaving generally spheroidal supported-liquid membranes having the ammonia-absorbing strongly acidic cation exchange resin substrate on the inside. BHK cells are grown in shaker flasks as described in the Reference Example. By including 10 ml of the so-prepared supported-liquid membrane beads per liter of culture medium, the ammonia formed during a 200-hour incubation period is continuously removed.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. A process removing ammonia formed during the culturing of mammalian cells in an aqueous culture medium by, (a) contacting said aqueous culture medium with one side of a two-sided, supported-fluid membrane wherein the membrane support is a microporous hydrophobic polymeric matrix; and (b) maintaining a strip solution in contact with the other side of said supported-fluid membrane, said strip solution comprising an aqueous solution having a pH $\leq 7.0$.

2. The process of claim 1 wherein said fluid of said supported-fluid membrane is a gas.

3. The process of claim 1 wherein said fluid is a liquid selected from dialkyl phosphoric acids, dialkyl alkylphosphonic acids, aryl sulfonic acids, alkyl sulfonic acids, aryl carboxylic acids, alkyl carboxylic acids, aryl alcohols, alkyl alcohols, aryl amines, alkyl amines, trialkylphosphine oxides, and solutions thereof.

4. The process of claim 1 wherein said microporous hydrophobic polymeric membrane support matrix is selected from at least one hollow fiber, at least one bead, and at least one coating on a bead substrate.

5. The process of claim 4 wherein said membrane support matrix is at least one hollow fiber and said aqueous culture medium is circulated in the lumens of said at least one hollow fiber.

6. The process of claim 4 wherein said at least one hollow fiber is potted into at least one module having inlet and outlet ports for said aqueous culture medium and for said strip solution.

7. The process of claim 4 wherein said at least one microporous hollow fiber is selected from a polymer comprising polypropylene, polytetrafluoroethylene, poly (vinylideneflouride), polysulfone, and polyethersulfone.

8. The process of claim 4 wherein said membrane support matrix is at least one coating on a bead substrate of ammonia-absorbing material.

9. The process of claim 8 wherein said bead substrate of ammonia-absorbing material is selected from a cation exchange resin and a hydrogen ion-containing porous ceramic.

10. The process of claim 1 wherein said aqueous culture medium is recycled for further use in culturing mammalian cells.

* * * * *